United States Patent [19]

Kunstmann et al.

[11] Patent Number: 5,714,586

[45] Date of Patent: *Feb. 3, 1998

[54] METHODS FOR THE PREPARATION OF MONOMERIC CALICHEAMICIN DERIVATIVE/CARRIER CONJUGATES

[75] Inventors: Martin P. Kunstmann, Pearl River; Irwin J. Hollander, Monsey; Philip Hamann, Garnerville; Arthur Kunz, New City, all of N.Y.

[73] Assignee: American Cyanamid Company, Madison, N.J.

[*] Notice: The term of this patent shall not extend beyond the expiration date of Pat. No. 5,712,374.

[21] Appl. No.: 654,505

[22] Filed: May 28, 1996

Related U.S. Application Data

[63] Continuation-in-part of Ser. No. 475,005, Jun. 7, 1995.
[51] Int. Cl.⁶ .......................... C07K 16/00; C12P 21/08; A61K 31/70; A61K 31/715
[52] U.S. Cl. .......................... 530/391.7; 514/25; 514/26; 514/53; 536/16.8
[58] Field of Search .......................... 530/391.7; 514/25, 514/26, 53; 536/16.8

[56] References Cited

U.S. PATENT DOCUMENTS

| | | | |
|---|---|---|---|
| 5,028,697 | 7/1991 | Johnson et al. | 530/391.1 |
| 5,053,394 | 10/1991 | Ellestad et al. | 514/25 |
| 5,094,849 | 3/1992 | Cullinan et al. | 530/390 |
| 5,461,068 | 10/1995 | Thaler et al. | 514/399 |

FOREIGN PATENT DOCUMENTS

| | | |
|---|---|---|
| 0313873 | 5/1989 | European Pat. Off. . |
| 0392384 | 10/1990 | European Pat. Off. . |
| 0689845 | 1/1996 | European Pat. Off. . |

OTHER PUBLICATIONS

Hinman, L. et al; Cancer Res. (1993), 53(14):3336–3342.

The Merk Index, An Encyclopedia of Chemicals, drugs, and Biologicals., Tenth edition., Merk & Co., Inc.pp.35 and 1130–1131, 1983.

Adam. A et al, Synthetic Adjuvants., John Wiley & Sons., pp. 137–138, 1985.

*Primary Examiner*—Ponnathapura Achutamurthy
*Assistant Examiner*—Padmashri Ponnaluri
*Attorney, Agent, or Firm*—Elizabeth M. Barnhard

[57] ABSTRACT

A method is provided for preparing monomeric calicheamicin derivative/carrier conjugates with higher drug loading/yield and decreased aggregation. These conjugates are prepared by incubating a calicheamicin derivative and a proteinaceous carrier in a solution comprising a non-nucleophilic, protein-compatible, buffered solution, a cosolvent selected from the group consisting of propylene glycol, ethanol, DMSO, and combinations thereof, and an additive comprising at least one $C_6$–$C_{18}$ carboxylic acid having a pH in the range from about 4.0 to 8.5 and at a temperature ranging from about 25° C. to about 37° C. for a period of time ranging from about 15 minutes to about 24 hours, and recovering monomeric calicheamicin derivative/carrier conjugates. Alternatively, the conjugates can be prepared by incubating the calicheamicin derivative and a proteinaceous carrier in a solution comprising a non-nucleophilic, protein-compatible, buffered solution and a cosolvent comprising t-butanol.

34 Claims, No Drawings

METHODS FOR THE PREPARATION OF MONOMERIC CALICHEAMICIN DERIVATIVE/CARRIER CONJUGATES

This is a continuation-in-part of copending application Ser. No. 08/475,005 filed on Jun. 7, 1995.

FIELD OF THE INVENTION

The present invention relates to methods for producing monomeric calicheamicin derivative/carrier conjugates.

BACKGROUND OF THE INVENTION

Since the discovery of methodology for producing monoclonal antibodies was published in the 1970's (G. Köhler and C. Milstein, *Nature* 256:495 (1975)), numerous attempts have been made to use these proteins selectively to target antitumor agents to tumors. (E.g., see T. Ghose and A. H. Blair, *CRC Critical Rev. Drug Carrier Systems* 3:263, 1987, G. A. Koppel, *Bioconjugate Chem.* 1:13, 1990, and J. Upeslacis and L. Hinman, *Ann. Rep. Med. Chem.* 23:151, 1988.) Although progress continues to be made in this field, most classical antitumor agents produce antibody conjugates which are relatively ineffective for a variety of reasons. Among the reasons for this ineffectiveness is the lack of potency of the chemotherapeutic.

The potent family of antibacterial and antitumor agents, known collectively as the calicheamicins or the LL-E33288 complex, are described in U.S. Pat. No. 4,970,198 (1990). The most potent of the agents is designated $\gamma_1^I$, which is herein referenced simply as gamma. These compounds contain a methyltrisulfide that can be reacted with appropriate thiols to form disulfides, at the same time introducing a functional group such as a hydrazide or other functional group that is useful in attaching a calicheamicin derivative to a carrier. Examples of this reaction with the calicheamicins are given in U.S. Pat. No. 5,053,394 which also discloses targeted forms of the calicheamicins.

A factor which has limited the use of the above-mentioned conjugates is their tendency to form aggregates when the amount of the calicheamicin derivative that is conjugated to the carrier (i.e., the drug loading) is increased. It is desirable to have as much drug loaded on the carrier as is consistent with retaining the affinity of the carrier protein, because higher drug loading increases the inherent potency of the conjugate. The presence of aggregate, which must be removed for therapeutic applications, also makes the scale-up of these conjugates more difficult and decreases the yield of the products. The amount of calicheamicin loaded on the carrier protein (the drug loading), the amount of aggregate that is formed in the conjugation reaction, and the yield of final purified monomeric conjugate that can be obtained are therefore all related. A compromise must therefore be made between higher drug loadings and the yield of the final monomer by adjusting the amount of the reactive calicheamicin derivative that is added to the conjugation reaction.

The tendency for calicheamicin conjugates to aggregate is especially problematic when the conjugation reactions are performed with the linkers described in European Patent Application No. 0689845. In this case, a large percentage of the conjugates produced are in an aggregated form that is quite difficult to purify further for therapeutic administration. For some carrier proteins, conjugates with even modest loadings are virtually impossible to make except on small scale. Therefore, there is a critical need for methods for conjugating cytotoxic drugs such as the calicheamicins to carriers which minimize that amount of aggregation and thereby allow for as high a drug loading as possible with a reasonable yield of product. The actual drug loading needed for good biological activity, the amount of aggregate that can be successfully removed during purification, and the final yield of conjugate that can be obtained need to be determined on a case-by-case basis.

SUMMARY OF THE INVENTION

The calicheamicin derivative/carrier conjugates of the present invention have the formula

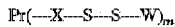

wherein:
Pr is a proteinaceous carrier,
X is a linker that comprises a product of any reactive group that can react with a proteinaceous carrier,
W is the calicheamicin radical formed by removal of the naturally occuring methyl trisulfide group; and
m is a number from 0.5 to 15.

A method of the present invention for preparing monomeric calicheamicin derivative/carrier conjugates with higher drug loading/yield and decreased aggregation comprises the steps of:

(1) incubating a calicheamicin derivative and a proteinaceous carrier in a non-nucleophilic, protein-compatible, buffered solution having an appropriate pH in the range from about 4.0 to 8.5 which solution further comprises (a) a cosolvent selected from the group consisting of propylene glycol, ethanol, DMSO, and combinations thereof, and (b) an additive comprising at least one $C_6$–$C_{18}$ carboxylic acid, wherein the incubation is conducted at a temperature ranging from about 25° C. to about 37° C. for a period of time ranging from about 15 minutes to about 24 hours; and (2) purification of the conjugate produced in step (1) to produce monomeric conjugates.

An alternative embodiment of the method of the present invention for preparing monomeric calicheamicin derivative/carrier conjugates with higher drug loading/yield and decreased aggregation comprises the steps of:

(1) incubating a calicheamicin derivative and a proteinaceous carrier in a non-nucleophilic, protein-compatible, buffered solution having an appropriate pH in the range from about 4.0 to 8.5 which solution further comprises the cosolvent t-butanol, wherein the incubation is conducted at a temperature ranging from about 25° C. to about 37° C. for a period of time ranging from about 15 minutes to about 24 hours hours and (2) purification of the conjugate produced in step (1) to produce monomeric conjugates.

DETAILED DESCRIPTION OF THE INVENTION

The conjugates of the present invention include a therapeutic agent derivatized with a linker that includes any reactive group that reacts with a proteinaceous targeting carrier. The use of particular cosolvents and additives induces the monomeric form as opposed to the aggregate form of these conjugates and allows for higher drug loading/yield without excessive aggregation. The monomeric form has therapeutic value.

Carriers

The carriers of the present invention preferably are proteinaceous carriers. Included as carrier molecules are growth factors, antibodies, antibody fragments, and their genetically or enzymatically engineered counterparts, hereinafter referred to singularly or as a group as carriers. The essential property of the carrier is its ability to recognize an antigen or receptor associated with undesired cells. Examples of carriers are given in U.S. Pat. No. 5,053,394, and such carriers are also appropriate in the present invention. Preferred carriers for use in the present invention are human or humanized antibodies.

Specific examples of carriers which are exemplified herein are the antibodies P67.6, A33, CT-M-01 (also known as 7F11C7) and the "anti-Tac" antibody of Waldman. These antibodies are used herein in two forms: a murine form, designated by an "m" (e.g., m-P67.6), and a genetically engineered, humanized form, designated by an "h" (e.g., h-P67.6) whenever appropriate. The basic technology for antibody humanization is disclosed by Winter in U.S. Pat. No. 5,225,539 (1993) and by Adair in PCT Publication NO. WO 91/09967 (1991). m-P67.6 is disclosed in I. D. Bernstein et al., *J. Clin. Invest.* 79:1153 (1987) and I. D. Bernstein et al., *J. Immunol.* 128:867–881 (1992) and recognizes the CD33 antigen which is prevalent on certain human myeloid tumors, especially acute non-lymphocytic leukemia (ANLL). Another antibody that can be used is MOPC-21, which is a non-targeting antibody, conjugates of which are useful as a control to show the targeting effects of other antibody conjugates. This murine antibody is disclosed in Melchers, F., *Biochem. J.* 119:765–772 (1970).

European Patent Application No. 0689845 discloses the DNA coding and predicted amino acid sequences of the variable regions of one particular h-P67.6 that is particularly preferred for use in the present invention. The framework for this antibody is the EU framework for human IgG$_4$ shown in Gottlieb et al., *Biochemistry* 9:3115 and 3161, 1970. The antibody was prepared using the general strategy described in PCT Publication No. WO 91/09967.

The antibody m-CT-M-01 is disclosed in European Patent Application No. 86401482.4/0208615 and recognizes the polyepithelial mucin (PEM) antigen present on many human solid tumors, particularly breast, lung, and ovarian tumors. The humanized version of this antibody, h-CT-M-01, is described in PCT Publication No. WO 93/06231 (1993). The antibody m-A33 is disclosed in U.S. Pat. Nos. 5,160,723 and 5,431,897 and is a murine antibody which recognizes a glycoprotein antigen present on colon cancer cells. The humanized version of this antibody, h-A33, is disclosed in PCT Patent Publication No. WO94/13805 (Jun. 23, 1994). Anti-Tac is disclosed in T. A. Waldman et al., *J. Immunol.* 126:1393 (1981), and is a murine antibody reactive with the IL-2 receptor that is found on activated and functionally mature T cells, including abnormally activated leukemia cells.

Therapeutic Agents

The therapeutic agents suitable for use in the present invention are cytotoxic antibiotics that bind to and disrupt DNA. Preferred cytotoxic agents are the calicheamicins which are methyl trisulfide antitumor antibiotics. Examples of calicheamicins suitable for use in the present invention are disclosed, for example, in U.S. Pat. No. 5,053,394. See also, U.S. Pat. Nos. 4,671,958; 4,970,198; 5,037,651; and 5,079,233. Preferred calicheamicins are gamma calicheamicin of N-acetyl gamma calicheamicins. The structure of N-acetyl gamma-calicheamicin in a conjugated form is illustrated below.

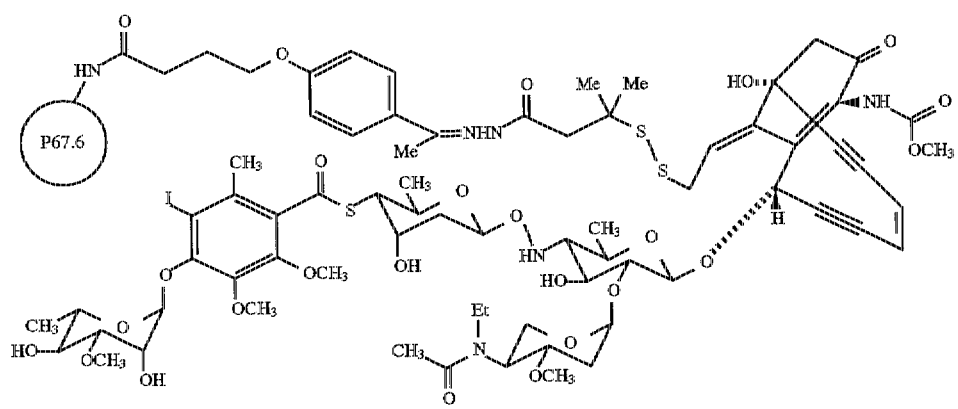

Calicheamicin Derivative/Carrier Conjugates

The conjugates of the present invention have the formula

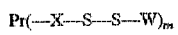

wherein:

Pr is a proteinaceous carrier,

X is a linker that comprises a product of any reactive group that can react with a proteinaceous carrier, W is the calicheamicin radical formed by removal of the naturally occuring methyl trisulfide group; and m is a number from 0.5 to 15.

Preferably, X has the formula Z-Sp wherein:

Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroaryl-aryl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, Sp can be additionally substituted by lower ($C_1$–$C_5$) dialkylamino, lower ($C_1$–$C_5$) alkoxy, hydroxy, or lower ($C_1$–$C_5$) alkylthio groups; and Z is —NHC(=O)—, —CH=NNHC(=O)—, —CH$_2$NHNHC(=O)—, —CH=NNHC(=O)NH—, —CH$_2$NHNHC(=O)NH—, —CH=NNHC(=S)NH—,
—CH$_2$NHNHC(=S)NH—, —CH=N—, —CH2NH—,
—OC(=O)—, —S—S—,

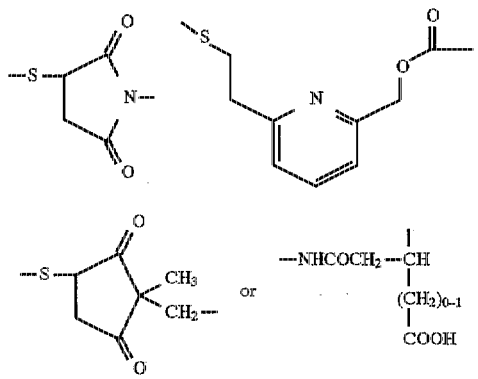

Alternatively, X has the formula

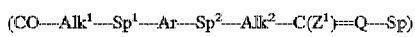

(CO—Alk$^1$—Sp$^1$—Ar—Sp$^2$—Alk$^2$—C(Z$^1$)=Q—Sp)

wherein

Alk$^1$ and Alk$^2$ are independently a bond or branched or unbranched (C$_1$-C$_{10}$) alkylene chain;

Sp$^1$ is a bond, —S—, —O—, —CONH—, —NHCO—, —NR'—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of (C$_1$-C$_5$) alkyl, (C$_1$-C$_4$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR', with the proviso that when Alk$^1$ is a bond, Sp$^1$ is a bond;

n is an integer from 0 to 5;

R' is a branched or unbranched (C$_1$-C$_5$) chain optionally substituted by one or two groups of —OH, (C$_1$-C$_4$) alkoxy, (C$_1$-C$_4$) thioalkoxy, halogen, nitro, (C$_1$-C$_3$) dialkylamino, or (C$_1$-C$_3$) trialkylammonium —A$^-$ where A$^-$ is a pharmaceutically acceptable anion completing a salt;

Ar is 1,2-, 1,3-, or 1,4-phenylene optionally substituted with one, two, or three groups of (C$_1$-C$_6$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

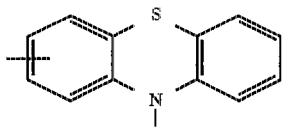

with each naphthylidene or phenothiazine optionally substituted with one, two, three, or four groups of (C$_1$-C$_6$) alkyl, (C$_1$-C$_5$) alkoxy, (C$_1$-C$_4$) thioalkoxy, halogen, nitro, COOR', —CONHR', —O(CH$_2$)$_n$COOR', —S(CH$_2$)$_n$COOR', or —S(CH$_2$)$_n$CONHR' wherein n and R' are as defined above, with the proviso that when Ar is phenothiazine, Sp$^1$ is a bond only connected to nitrogen;

Sp$^2$ is a bond, —S—, or —O—, with the proviso that when Alk$^2$ is a bond, Sp$^2$ is a bond;

Z$^1$ is H, (C$_1$-C$_5$) alkyl, or phenyl optionally substituted with one, two, or three groups of (C$_1$-C$_5$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined above;

Sp is a straight or branched-chain divalent or trivalent (C$_1$-C$_{18}$) radical, divalent or trivalent aryl or heteroaryl radical, divalent or trivalent (C$_3$-C$_{18}$) cycloalkyl or heterocycloalkyl radical, divalent or trivalent aryl- or heteroarylaryl (C$_1$-C$_{18}$) radical, divalent or trivalent cycloalkyl- or heterocycloalkyl-alkyl (C$_1$-C$_{18}$) radical or divalent or trivalent (C$_2$-C$_{18}$) unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocourmarinyl, or phenazinyl and wherein if Sp is a trivalent radical, Sp can be additionally substituted by lower (C$_1$-C$_5$) dialkylamino, lower (C$_1$-C$_5$) alkoxy, hydroxy, or lower (C$_1$-C$_5$) alkylthio groups; and Q is =NHNCO—, =NHNCS—, =NHNCONH—, =NHNCSNH—, or =NHO—.

Preferably, Alk$^1$ is a branched or unbranched (C$_1$-C$_{10}$) alkylene chain; Sp$^1$ is a bond, —S—, —O—, —CONH—, —NHCO—, or —NR' wherein R' is as hereinbefore defined, with the proviso that when Alk$^1$ is a bond, Sp$^1$ is a bond;

Ar is 1,2-, 1,3-, or 1,4-phenylene optionally substituted with one, two, or three groups of (C$_1$-C$_6$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as hereinbefore defined, or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of (C$_1$-C$_6$) alkyl, (C$_1$-C$_5$) alkoxy, (C$_1$-C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR'.

Z$^1$ is (C$_1$-C$_5$) alkyl, or phenyl optionally substituted with one, two, or three groups of (C$_1$-C$_5$) alkyl, (C$_1$-C$_4$) alkoxy, (C$_1$-C$_4$) thioalkoxy, halogen, nitro, COOR', —CONHR', —O(CH$_2$)$_n$COOR', —S(CH$_2$)$_n$COOR', —O(CH$_2$)$_n$CONHR', or —S(CH$_2$)$_n$CONHR';

Alk$^2$ and Sp$^2$ are together a bond; and

Sp and Q are as immediately defined above.

Calicheamicin derivatives can, for example, be attached to lysine residues of the antibody. Lysine attachment as disclosed in U.S. Pat. No. 5,053,394 produces conjugates which are stable to hydrolysis under normal physiological conditions.

U.S. Pat. No. 5,053,394 also discloses conjugates where a nucleophilic calicheamicin derivative, such as a hydrazide, is reacted with periodate oxidized carbohydrates on an antibody under mildly acidic conditions. This produces a Schiff base or derivative thereof, such as a hydrazone, which can be further reduced with, e.g., cyanoborohydride, if desired, to produce a hydrolytically stable conjugate.

European Patent Application No. 0689845 discloses other linkers that can be used with nucleophilic derivatives, particularly hydrazides and related nucleophiles, prepared from the calicheamicins. These linkers are useful in those cases (e.g., P67.6), where better activity is obtained when the linkage formed between the drug and the linker is hydrolyzable. These linkers contain two functional groups. One group typically is a carboxylic acid that is utilized to react with the carrier. The acid functional group, when properly activated, can form an amide linkage with a free amine group of the carrier, such as, for example, the amine in the side chain of a lysine of a monoclonal antibody carrier. The other functional group commonly is a carbonyl group, i.e., an aldehyde or a ketone, which will react with the appropriately modified therapeutic agent. The carbonyl groups can react with a hydrazide group on the drug to form a hydrazone linkage. This linkage is hydrolyzable at the target cell to release the therapeutic agent from the conjugate.

A most preferred bifunctional linker for use in the present invention is 4-(4-acetylphenoxy) butanoic acid (AcBut), which results in a preferred product where the conjugate consists of gamma calicheamicin or N-acetyl gamma calicheamicin functionalized by reacting with the hydrazide of 3-mercapto-3-methyl butanoic acid, the linker 4-(4-acetylphenoxy)butanoic acid (AcBut), and a human or humanized monoclonal antibody targeting carrier.

Monomeric Conjugation

The natural hydrophobic nature of the calicheamicins creates difficulties in the preparation of monomeric conjugates with good drug loadings and reasonable yields which are necessary for clinical applications. The increased hydrophobicity of the linkage provided by linkers, such as the AcBut linker, disclosed in European Patent Application No. 0689845, as well as the increased covalent distance separating the therapeutic agent from the monoclonal antibody (MoAb), exacerbate this problem.

Aggregation of calicheamicin/carrier conjugates with higher drug loadings occurs due to the hydrophobic nature of the calicheamicins. The drug loading often has to be limited to obtain reasonable quantities of monomeric product. In some cases, such as with the conjugates in European Patent Application No. 0689845, it is often impossible to make conjugates in useful yields with useful loadings for therapeutic applications using the reaction conditions disclosed in U.S. Pat. No. 5,053,394 due to excessive aggregation. These reaction conditions utilized DMF as the cosolvent in the conjugation reaction. Methods which allow for higher drug loadings/yield without aggregation and the inherent loss of material are therefore needed.

For humanized carriers including, but not limited to, proteins such as human or humanized monoclonal antibodies that are used to target the cytotoxic therapeutic agents herein, such as, for example, P67.6 and the other humanized monoclonal antibodies disclosed herein, use of a non-nucleophilic, protein-compatible, buffered solution containing (i) propylene glycol (PG) as a cosolvent and (ii) an additive comprising at least one $C_6$–$C_{18}$ carboxylic acid was found to produce monomeric calicheamicin derivative/carrier conjugates with higher drug loading/yield and decreased aggregation having excellent activity. Preferred acids are $C_7$ to $C_{12}$ acids, and the most preferred acid is octanoic (caprylic) acid (CA). Preferred buffered solutions for conjugates made from OSu esters or other comparably activated esters are phosphate-buffered saline (PBS) or N-2-hydroxyethyl piperazine-N'-2-ethane sulfonic acid (Hepes buffer), while preferred buffered solutions for conjugates made from the oxidized carbohydrates of antibodies is sodium acetate. The buffered solution used in these conjugation reactions cannot contain free amines or nucleophiles. Acceptable buffers for other types of conjugates can be readily determined by those who are skilled in the art. Alternatively, the use of a non-nucleophilic, protein-compatible, buffered solution containing t-butanol without an additive was also found to produce monomeric calicheamicin derivative/carrier conjugates with higher drug loading/yield and decreased aggregation.

The amount of cosolvent used is a monomeric conjugating effective amount and can be determined by those of ordinary skill in the art without undue experimentation. The amount of additive is a monomeric conjugation enhancing effective amount. This amount can also be determined by one of ordinary skill in the art without undue experimentation. Additions of propylene glycol (PG) in amounts ranging from about 10% to about 60%, preferably about 10% to about 40%, and most preferably about 30% by volume of the total solution, and an additive comprising at least one $C_6$–$C_{18}$ carboxylic acid, preferably caprylic acid, in amounts ranging from about 20 mM to about 100 mM, preferably from about 40 mM to about 90 mM, and most preferably about from 60 mM, are added to conjugation reactions to produce monomeric calicheamicin derivative/carrier conjugates with higher drug loading/yield and decreased aggregation. Some or all of the PG cosolvent is used to transfer the drug into the conjugation mixture. When the cosolvent used for drug transfer amounts to 10% or less of the total volume of the conjugation mixture, it can optionally be substituted by ethanol or DMSO.

Alternatively, the concentration of the $C_6$–$C_{18}$ carboxylic acid, preferably caprylic acid, can be increased to 150–300 mM and the cosolvent dropped to 1–10% propylene glycol, ethanol, or DMSO, and is preferably 200 mM caprylic acid and 5% propylene glycol or ethanol.

In another alternative, t-butanol at concentrations ranging from about 10% to about 25%, preferably about 15%, by volume of the total solution may be added to the conjugation reaction to produce monomeric calicheamicin derivative/carrier conjugates with higher drug loading/yield and decreased aggregation.

In the foregoing reactions, the concentration of MoAb ranges from about 1 to about 15 mg/ml and the concentration of the drug, e.g., AcBut calicheamicin, ranges from about 0.025 to about 1 mg/ml. The reactions are performed in PBS or acetate buffer at a pH of from about 4.0 to about 8.5, depending on the type of conjugate being made, at a temperature ranging from about room temperature (25° C.) to about 37° C. for times ranging from about 15 minutes to about 24 hours. The conjugates may be recovered and purified by conventional methods, for example, HPLC, FPLC or SEPHACRYL S-200™. The purified conjugates are monomeric and contain from about 2 to about 6 moles/mole drug/MoAb.

The addition of cosolvent and/or the additive may alter the pH of the buffered solution so that it may be necessary to adjust the pH of the solution to the preferred pH range of about 4.0 to 8.5. Preferably, the pH of the buffered solution containing the cosolvent and the additive will be about 7.0 to 8.5 for conjugates made from OSu esters, or about 4.0 to 6.5 for conjugates made from the oxidized carbohydrates of the antibody. Most preferably, the pH of the buffered solution containing the cosolvent and the additive will be about 7.7 for conjugates made from OSu esters, or about 5.5 for conjugates made from the oxidized carbohydrates of the antibody. Acceptable pH ranges for other types of conjugates can be readily determined by those who are skilled in the art.

For various murine monoclonal antibodies the use of other combinations of the aforementioned additives have been found to improve drug loading and monomeric conjugate yield, and it is understood that any particular protein carrier may require some minor alterations in the exact conditions or choice of additives to achieve the optimum results.

DESCRIPTION OF THE PREFERRED EMBODIMENTS

The present invention is further described below in specific working examples which are intended to further describe the invention without limiting its scope.

EXAMPLE 1

Conjugations in DMF: Variations in DMF Concentration, Drug/protein Ratio and Buffers Employed The first set of experiments were performed with N-acetyl gamma calicheamicin functionalized by reacting with the hydrazide of 3-mercapto-3-methyl butanoic acid attached to the linker 4-(4-acetylphenoxy)butanoic acid and activated as the OSu ester (herein referred to as AcBut calicheamicin) on both murine and human P67.6 with variations in DMF concentrations, drug/protein ratio, and buffer. The results indicated that these "standard" conditions produce monomeric conjugate in 20–30% yield due to a loss of material as aggregate with a drug loading of 1.5–3 moles drug per mole protein and therefore alternate conditions were required.

To a protein solution of 4.5–5 mg/mL protein in PBS buffer (50 mM sodium phosphate, 100 mM NaCl, pH 7.4) was added 6 molar equivalents of drug in DMF (3.3 mg/mL) with additional DMF for a final concentration of 25% DMF. This was incubated at room temperature overnight with gentle shaking. The conjugated protein was then purified by either FPLC Superose™ for volumes <0.5 mL and by SEPHACRYL S-200™ for larger volumes.

For mP67.6 (large scale), this resulted in only 32% protein yield of monomer with drug loading of 1.9 M/M. For hP67.6, monomeric protein yield was 26% with drug loading of 2.9 M/M. Thus, although drug loadings on monomer were acceptable, the difficult purification and the low yields due to the loss of material as aggregate were considered unacceptable for further development and scale-up.

A study was done to compare drug loadings vs. monomer yield in 30% DMF using hP67.6 in PBS pH 7.4, and various equivalents (5–9.5 M/M) of drug. All samples were incubated at room temperature overnight, exchanged into PBS on PD10 columns, and analyzed by spectrophotometry for protein recovery and drug loading. Samples were further analyzed by HPLC on Zorbax™ GF-250 in 0.2M sodium phosphate, pH 7, and Superose™ 12 in PBS, pH 7.4. This was followed by purification on FPLC Superose™ in PBS. Results: maximum loading obtainable was 3–3.5 M/M but with low yield (<20%).

A similar loading study as above was performed but Hepes buffer (100 mM, pH 7) was substituted for the PBS buffer. Results: no difference except that aggregate appeared to precipitate or stick to the column and was therefore not seen during final purification. This was followed by a loading study as above, but with 0.5M NaClO4 added to the buffer. This was done to serve as a possible solubilizing agent for the drug. Results: no obvious benefit.

An additional study was then performed in Hepes buffer (50 mM, pH 7.4) rather than PBS. Results: no obvious benefit.

EXAMPLE 2

Optimization for Humanized Antibodies

Experiments to Dissociate Aggregate

At this point no improvement over the initial methodology had been found. The possibility that conditions that caused a reduction in the amount of aggregate might allow increases in drug loading and/or higher yields of purified monomer was investigated. Since all indications were that the aggregated conjugates were associative, not covalent, and probably caused by hydrophobic interactions, it was hypothesized that studying their properties would be informative. Thus, experiments were first performed to find additives that could break up preformed aggregate. It was assumed that anything that had such activity might also serve to prevent aggregation (and thus increase yield of monomer) if used during the conjugation. The reagents used were chosen based on their FDA approved safety as drug additives, their potential effect for solubilizing hydrophobic moieties, and/or their compatibility with proteins. These studies led to the identification of three potentially useful additives.

Twelve permutations of different additives were used to disassociate aggregate. An aggregate fraction from a hP67.6-AcBut calicheamicin conjugation purification containing ~25% dimer was concentrated to 0.7 mg/mL protein. Various additives were added to aliquots of the dimer-rich hP67.6-AcBut: PBS, 0.3M glycine, 0.2M glycine+2% maltose, 0.1M glycine+0.1M histidine, 1% Pluronic F-68, 80 mM caprylic acid (octanoic acid), 40 mM caprylic acid+6 mM N-acetyl-tryptophan, 1% benzyl alcohol, 0.5% sodium benzoate, 33% propylene glycol, and 25% glycerol. Each treated aliquot was incubated at room temperature overnight and then analyzed by gel-filtration HPLC on Zorbax™ GF-250 and on Superose™ 12 using dual detectors at 280 and 333 nm. Analysis was done for both aggregate (or dimer)-to-monomer ratio and for total recovery of monomer. Results: propylene glycol (PG), caprylic acid (CA) and glycerol were better than other additives in reducing dimer without reducing recovery of protein. They reduced aggregates by 50–90% while other additives had almost no effect.

EXAMPLE 3

Conjugations Using Disaggregation Additives

Based on these results, PG, CA and glycerol were used during conjugation. In addition, isopropanol and t-butanol were tried as well. Isopropanol and t-butanol have been used as cosolvents at low percentages with proteins with no harm (personal observations).

Conjugation of hP67.6 to AcBut-calicheamicin was performed in the presence of 25% PG, 80 mM CA, 25% glycerol, 25% isopropanol (IPA), 25% t-butanol, or 25% PG+80 mM CA. All were done with 3.25 mg/mL protein (final) in PBS, pH 7.4, and 6 moles drug per mole MoAb. All were compared to a control conjugation performed in 25% DMF while all the test solutions contained ~5% DMF from the drug stock. Conjugation was also done with 4M/M drug in 25% PG or 25% DMF as control. All samples were incubated at room temperature overnight, exchanged into PBS on PD10 columns, and analyzed by spectrophotometry for protein recovery and drug loading. Samples were further analyzed by HPLC on Zorbax™ and Superose™. Following the conjugation reaction, the conjugates were purified on FPLC Superose™. Results: All of these additives seemed beneficial except glycerol (low loading). PG+CA seemed best in terms of conjugate yield, drug loading and minimizing aggregate.

Thus, a series of studies investigating the combination of CA to other additives, optimization of PG concentration, and direct comparisons with t-BuOH followed.

Since CA added to PG seemed to improve protein recovery, drug loading and minimize aggregation as discussed above, conjugation was performed on hP67.6 using PG, t-BuOH, or IPA (each at 25%), each with and without CA (80 mM) to see if CA can synergize with other additives. Conditions and analysis were as above. Results: t-BuOH and CA were incompatible at these concentrations, while IPA was not as good as PG in improving yield and decreasing aggregate.

Conjugations were performed to optimize the PG+CA conditions where PG was used at 10, 15, or 20% and CA at 40 or 80 mM. Analysis was as above. Results: 20% PG and 80 mM CA appeared best, producing loading of 3–3.8 with recovery of >60%. Conclusion: t-BuOH was effective as an alternative to PG/CA and therefore more experiments were performed to confirm this observation and to optimize the conditions for t-BuOH use.

Conjugates were performed with hP67.6 in PBS using 5–20% t-BuOH and 6–10 equivalents of drug. Results: 10% t-BuOH appears sufficient with 6 equivalents of drug to produce conjugates with a loading of 2.3 M/M with little aggregate in the crude product. Hepes buffer as a substitute for PBS shows no benefit.

Conjugations were performed comparing propylene glycol (PG) at 20% and 80 mM caprylic acid (CA) vs. 15% t-BuOH. Each was tested with 6, 9, and 12 moles of drug per mole hP67.6 in PBS. Results: the combination of PG+CA seemed better in terms of protein recovery for producing higher loading, while both methods were about the same for lower loadings.

At this point, using 20% PG with 80 mM CA was a somewhat better additive than 15% t-BuOH but both were major improvements over the original conditions. However, while t-BuOH had no effect on the pH of the protein in PBS, the PG dropped the pH from 7.4 to ~6.9. This was related to the observation that the t-BuOH reactions were complete in 1–3 hours while the PG/CA reactions took overnight.

EXAMPLE 4

Conjugations in PG/CA With pH Variance

A series of conjugations were performed with 30% PG/80 mM CA with and without adjustment of pH to 7.4. Also, conjugations were done using 25% vs. 30% t-BuOH, in the absence of DMF. Results: pH adjustment produced better incorporation of drug.

It was clear that conjugation in PG+CA with the pH readjusted to 7.4 produced far better yields than conjugation in t-BuOH for generating conjugates with high loading. For loadings of ~2 M/M, the two methods produced similar yields but as loadings were increased by increasing the drug/protein ratio during conjugation, yields using t-BuOH were significantly reduced to as little as 25% of the yield obtained with PG/CA (e.g., loadings of 5 M/M).

EXAMPLE 5

Large Scale Preparations

Large scale preparations (using 20–40 mg protein rather than the 0.5–1 mg per sample utilized on experimental scale) were attempted. The goal was to determine the applicability of the new conditions during scale-up and also to produce conjugates with a range of drug loading. These conjugates were tested in vivo on xenograft tumors to confirm that the additives allow production of effective conjugates and that higher loaded conjugates are more effective than lower loaded ones.

A large scale prep of hP67.6-AcBut was made (30 mg of protein used) using only 4 mole equivalents of drug and 20% PG/80 mM CA, 5% DMF, pH adjusted to 7.5. Far less aggregate was formed under these conditions than in original preparations. Final purified monomer had 1.9 M/M drug with a protein yield of 67%.

To get higher drug loading, the same conditions were followed but with 9 equivalents drug used for conjugation rather than 6. This resulted in only slightly more aggregation but yielded monomeric conjugate with 3.2 M/M drug loading and protein yield only slightly down to ~60%.

The large scale (30 mg protein) preparations, although vastly improved over initial results, still produced 30–40% less loading than expected based on the small scale work. It was suspected that the slightly increased DMF used in large scale work had caused this problem. Thus numerous small scale studies were performed over a range of DMF concentrations to confirm this.

EXAMPLE 6

Effect of Small Amounts of DMF During Conjugation

Conjugations were performed in 10% t-BuOH with 4 M/M drug while varying the DMF concentration from 1% to 7%. Here the drug stock was 10 mg/mL DMF to allow low DMF concentrations during conjugation. Results: Increasing amounts of DMF seemed to lower incorporation of drug.

Small scale conjugations were performed using 6.4 M/M drug and 30% PG/80 mM CA, but using DMF at 0 and 8% vs. 25% t-BuOH with 2% and 8% DMF. Drug stocks were made in PG to better control DMF concentrations. Results: DMF was found to increase aggregation (and thus decrease monomer yield) in both PG/CA and t-BuOH (more so in PG/CA) and again PG/CA was better than t-BuOH for conjugations.

A large scale prep was performed without DMF to confirm the small scale results. Conjugation was begun at 30% PG/80 mM CA and 6.1 M/M drug. Aliquots were tested and indicated that these conditions had produced a loading of 3.2 M/M as expected based on small scale, confirming the need to avoid DMF as a cosolvent.

This conjugation was treated with an additional 3 equivalents of drug which produced a final purified monomer with a drug loading of 4.4 M/M and protein yield of 46%.

Thus, three large scale preparations had been completed to produce conjugates with drug loadings of 1.9, 3.2, and 4.4 moles drug per mole protein. These were evaluated in vitro and in vivo. The combination of PG and CA were the best reaction additives, while DMF was detrimental to the reaction.

EXAMPLE 7

Final Optimizations

A series of tests were performed to find optimal concentrations of PG and CA, optimal pH, order of addition and substitutes for DMF as drug solvents.

Small-scale conjugations were performed in 30% PG/80 mM CA but with varying orders of addition of MoAb, PG, CA, and of drug stock made up in PG, EtOH, or DMSO. Results: best order of addition was MoAb, then PG, then CA (pH adjusted), then drug stock made up in PG. EtOH and DMSO were both acceptable alternatives to using PG for the drug stock.

A conjugation study was performed using 40, 55, 75 and 80 mM CA, all with 25% PG. Results: 55 mM CA was found best in terms of protein yield and drug loading.

Another conjugation study was performed with 40, 50, 60 and 70 mM CA with 25% PG. Results: 60 mM CA was found best in terms of protein yield and drug loading.

A conjugation study with 25% PG+80 mM CA and 0, 2, or 4% DMF was performed. This was to see if low levels of DMF are harmful. Results: no great differences, thus only concentrations above 4% must be problematical.

Conjugations were performed with variation in rate of stirring during conjugation. Results: no differences seen.

Conjugation was performed with drug added in EtOH instead of PG. Results: no significant change from using drug in PG.

A series of conjugations were performed in PG/CA and 6 M/M drug but with variation in pH from 7.0 to 8.5. Progress of the reaction and extent of loading was monitored by measurement of reactants and hydrolysis products (using RP-HPLC). Results: all experiments indicated that the higher the pH, the faster the reaction, ranging from 12 hours at pH 7 to <45 minutes at pH 8.5. It was decided that a pH of >7.5 produces the highest yield and load.

The same procedure using PG/CA additives was utilized for conjugation of AcBut-calicheamicin to two other humanized MoAbs, CT-M-01 and A33. Similar loadings and yields seen in the use of humanized P67.6 both on small and large scale was obtained for these humanized MoAbs as well.

EXAMPLE 8

AcBut-calicheamicin was conjugated to 5 mg of humanized CT-M-01 monoclonal antibody in the presence of 25% propylene glycol (PG) and 80% caprylic acid. The reaction was performed overnight (approximately 24 hours) at room temperature (25° C.). The product was analyzed by HPLC.

Results: 75% monomer with drug loading of 1.9 M/M.

EXAMPLE 9

AcBut-calicheamicin was conjugated to 36.6 mg hCT-M-01 monoclonal antibody in the presence of 30% PG and 60 mM CA. The reaction was performed for 2 hours at about 25° C. The product was analyzed by HPLC.

Results: 60% monomer with a drug loading of 2.2 M/M.

EXAMPLE 10

AcBut-calicheamicin was conjugated to 1 mg humanized A33 MoAb in the presence of 30% PG and 60 mM CA.

Results: Approximately 50% monomer with a drug loading of 1.8 M/M. Past experience has shown us that hA33 is a difficult protein to work with due to the pronounced tendency of its conjugates to aggregate.

EXAMPLE 11

AcBut-calicheamicin was conjugated to 50 mg of hP67 in the presence of 200 mM CA and 5% ethanol (from the drug stock). Incubation was for 2 hours at 25° C.

Results: ~95% monomer with a drug loading of 2.1 M/M and a protein yield of 65%.

It was thus found that good results can be obtained when the CA concentration is increased dramatically and the cosolvent is decreased.

EXAMPLE 12

Final Procedure for Humanized Antibodies

Based on all of the above results, a final procedure recommended for use in development of hP67.6 conjugation to AcBut-calicheamicin was as follows: Five stock solutions were used: hP67.6 at ~6.5 mg/mL in PBS (50 mM sodium phosphate, 100 mM NaCl, pH 7.4), propylene glycol (PG), 1M NaOH, 1M caprylic acid (CA) in PBS, pH 7.4, and drug in PG (~6 mg/mL). The final concentrations during conjugation were: 30% PG (5% of the PG was from the drug stock), 60 mM CA, approximately 4 mg/ml p67.6, and 6 moles drug per mole of hP67.6. PG was added to the hP67.6 and mixed thoroughly. The CA was added and mixed thoroughly. Alternatively, CA was added to 200 mM final concentration and 5% PG (or EtOH) was obtained from addition of the drug (the AcBut-calicheamicin). The pH was adjusted by addition of ~10 mL NaOH/mL of solution to obtain a pH of 7.7–7.8. The drug was then added and the solution mixed vigorously. The solution was incubated at 25° C. with shaking for 3 hours followed by filtration through Millex HV filters to remove insoluble material. The conjugate was then purified by gel filtration on SEPHACRYL S-200™ in PBS (pH 7.4) using no more than a ~1% load or, for small conjugations <0.5 mL, Superose™ 12 FPLC in PBS was utilized. Final monomeric (<4% dimer) conjugate was produced in >60% protein yield with a drug loading of >2.5 moles drug/mole protein.

This procedure appeared to be effective on the three humanized MoAbs tested: A33, CT-M-01, and P67.6, which are of two different isotypes ($IgG_1$, $IgG_4$, and $IgG_4$, respectively).

EXAMPLE 13

Optimization of Conditions for Murine Antibodies

The same procedures when applied to murine MoAbs did show improvements over the use of just DMF alone as co-solvent, but were in general less effective in preventing aggregation than with the humanized antibodies, as can be seen by the examples which follow. The results also vary greatly for each MoAb, again illustrating that the best conjugation procedure varies for each calicheamicin/carrier conjugate, but that variations of the general procedures suggested in the present patent show significant improvements in all cases examined over the results achieved with DMF as the only co-solvent.

Conjugations using the PG/CA procedures described above produced the following loadings:

| MoAb | Loading (M/M) |
|---|---|
| Anti-Tac | 0.7 |
| M5/114 | 1.2 |
| Campath II | 1.4 |
| MN-1 | 1.2 |
| LC-1 | 1.0 |
| LK-26 | 1.2 |
| TH-69 | 1.0 |
| A33 | 1.1 |

Protein yields were modest, ranging from 20 to 40%. When mA33 was conjugated using 8 M/M drug, final loading on monomer was only 1.1–1.3 M/M. The anti-Tac conjugate, with a loading of 0.7 m/M, was reconjugated in the presence of 20% t-BuOH since that was the best backup additive. This increased loading to 2.0 M/M but in only 23% yield.

Conjugations Using PG+t-BuOH

Although the PG/CA system produced only modest improvements with the above mentioned MoAbs, the use of t-BuOH/(t-Bu/PG) PG seemed promising. The following studies describe conjugations in which PG and t-BuOH were used in combination. This led to the conclusion that a PG/t-BuOH system was better suited for these murine MoAbs while the PG/CA system was better for humanized MoAbs that were examined.

Conjugations were performed with variations in t-BuOH and PG concentrations. It was found that PG was useful in solubilizing (clarifying) conjugation solutions for many murine MoAbs in the presence of AcBut calicheamicin and t-BuOH. When anti-Tac was conjugated in 20% t-BuOH, 10% PG, and 6 M/M drug, the final monomer had drug loading of 1.3 M/M with a 40% yield. When done in 15% t-BuOH, 15% PG, and 6.7 M/M drug, the product had drug loading of 1.4 M/M and a 50% yield, a slight improvement over the previous attempt but distinctly better than the 0.7 M/M loading and ~20% yield obtained in PG/CA. When the same conditions were followed but with protein concentration increased to 2.8 mg/mL (from ~2) final drug loading increased to 2.2 M/M.

For mA33, a protein that is routinely difficult to work with, no conditions were found that could bring loading significantly above 1.0 M/M but the above combination of t-BuOH and PG (with 8 M/M drug) produced conjugate in 60% yield even on large scale. Three $IgG_1$ murine MoAbs (that would presumably have similar chemical reactivities) MOPC, M44, and M67, when conjugated under essentially identical conditions (15% t-BuOH, 10-20% PG, 6.7 M/M drug) all produced monomer with loading ~1.0, but in yields ranging from 14-45%. For MOPC, increasing protein concentration to 2.8 mg/mL (as with anti-Tac) and using 8 M/M drug in the 15% t-BuOH, 20% PG buffer system increased drug loading to 1.7 M/M in ~50% yield.

Final Procedure for Murine Antibodies

Based on this series of conjugations, the recommended procedure for conjugation of these murine MoAbs is substantially different than that for the humanized MoAbs that were examined. Additionally, the optimized protein yields and drug loadings obtained vary considerably among the different murine MoAbs tested, indicating that some optimization of conditions may be required to find the best conditions for any particular protein carrier.

PBS, pH 7.4, was utilized as the buffer but the MoAb stock was at 4 to 5.5 mg/mL. t-BuOH was used as an additional cosolvent, but not CA. The drug stock (8-10 mg/mL) was made in DMSO or DMF. Final reaction conditions were 15% t-BuOH, ~20% propylene glycol (or more if needed to clarify the solution), 2-4% DMSO (from the drug stock), and 6-8 moles drug/mole protein. The conjugation proceeded with incubation at 25° C. with shaking for 3 to 20 hours. Purification was as described above for humanized conjugates. Final protein yields ranged from 25% to 60% and drug loading from 1 to 2.2 moles of drug per mole of MoAb, depending on the individual MoAb.

EXAMPLE 14

Effect of tBuOH on Carbohydrate Conjugates

MOPC-21 was oxidized in pH 5.5 acetate buffer with 15 mM $NaIO_4$ at ambient temperature for 45 minutes. The buffered was then exchanged for fresh acetate buffer to remove the spent oxidation reagents. A portion of this oxidized antibody was treated with the disulfide resulting from the reaction of N-acetyl gamma-calicheamicin with the hydrazide of 3-mercapto-3-methyl butanoic acid (GAD) in the presence of 15% DMF. A second portion was treated with the same concentration of GAD in the presence of 5% DMF and 15% tBuOH. Both reactions were allowed to proceed at ambient temperature for 17 hours. Each reaction then had the buffer exchanged for pH 7.4 PBS. The amount of aggregate in the conjugation reaction with tBuOH was less than that in the reaction with only DMF (4.1% versus 7.3%). After purification by gel-exclusion chromatography the conjugate from the reaction with only DMF had a loading of 3.2 M/M with 3% residual aggregate while the conjugate made in the presence of tBuOH had a loading of 5.1 M/M with no detectable residual aggregate.

EXAMPLE 15

Effect of PG/CA on the Formation of a Non-Hydrolysable Conjugate h-CT-M-01 was treated with the OSu ester of the disulfide resulting from the reaction of N-acetyl gamma-calicheamicin with 4-mercapto-4-methyl pentanoic acid in the presence of 15% DMF in Hepes buffer. A second conjugation was performed with 30% PG and 80 mM CA instead of DMF. Both reactions were allowed to proceed at ambient temperature for 2 hours. Each reaction then had the buffer exchanged for pH 7.4 PBS. Although the amount of aggregate (~2%) and the loading (3.95 M/M with DMF versus 4.12 M/M with PG+CA) was comparable for both reactions, the estimated yield was higher for the reaction run in the presence of PG+CA (60% versus 50%).

All patents, applications, articles, publications, and test methods mentioned herein are hereby incorporated by reference.

Variations of the present invention will suggest themselves to those skilled in the art in light of the above detailed description. Such obvious variations are within the full intended scope of the appended claims.

What is claimed is:

1. A method for preparing monomeric calicheamicin derivative/carrier conjugates with higher drug loading/yield and decreased aggregation having the formula,

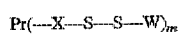

wherein:
Pr is a proteinaceous carrier,
X is a linker that comprises a product of any reactive group that can react with a proteinaceous carrier,
W is the calicheamicin radical formed by removal of the naturally occurring methyl trisulfide group, and
m is a number from 0.5 to 15;
said method comprising the steps of:
(1) incubating a calicheamicin derivative (X—S—S—W) and a proteinaceous carrier (Pr) in a non-nucleophilic, protein-compatible, buffered solution having a pH in the range from about 4.0 to 8.5 which solution further comprises (a) a cosolvent selected from the group consisting of propylene glycol, ethanol, DMSO, and combinations thereof, and (b) an additive comprising at least one $C_6$-$C_{18}$ carboxylic acid, wherein the incubation is conducted at a temperature ranging from about 25° C. to about 37° C. for a period of time ranging from about 15 minutes to about 24 hours to produce a calicheamicin derivative/carrier conjugate; and
(2) purifying the calicheamicin derivative/carrier conjugate produced in step (1) to produce a monomeric calicheamicin derivative/carrier conjugate.

2. The method of claim 1, wherein X has the formula Z—Sp wherein:

Sp is a straight or branched-chain divalent or trivalent $(C_1–C_{18})$ radical, divalent or trivalent aryl or heteroaryl radical, divalent or trivalent $(C_3–C_{18})$ cycloalkyl or heterocycloalkyl radical, divalent or trivalent aryl- or heteroaryl-aryl $(C_1–C_{18})$ radical, divalent or trivalent cycloalkyl- or heterocycloalkyl-alkyl $(C_1–C_{18})$ radical or divalent or trivalent $(C_2–C_{18})$ unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, Sp can be additionally substituted by lower $(C_1–C_5)$ dialkylamino, lower $(C_1–C_5)$ alkoxy, hydroxy, or lower $(C_1–C_5)$ alkylthio groups; and Z is —NHC(=O)—, —CH=NNHC(=O)—, —CH$_2$NHNHC(=O)—, —CH=NNHC(=O)NH—, —CH$_2$NHNHC(=O)NH—, —CH=NNHC(=S)NH—, —CH$_2$NHNHC(=S)NH—, —CH=N—, —CH2NH—, —OC(=O)—, —S—S—,

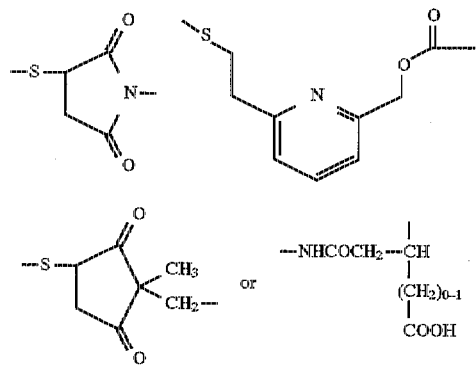

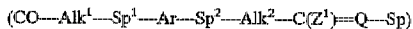

3. The method of claim 1, wherein X has the formula (CO—Alk$^1$—Sp$^1$—Ar—Sp$^2$—Alk$^2$—C(Z$^1$)=Q—Sp)

wherein

Alk$^1$ and Alk$^2$ are independently a bond or branched or unbranched $(C_1–C_{10})$ alkylene chain;

Sp$^1$ is a bond, —S—, —O—, —CONH—, —NHCO—, —NR'—, —N(CH$_2$CH$_2$)$_2$N'—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of $(C_1–C_5)$ alkyl, $(C_1–C_4)$ alkoxy, $(C_1–C_4)$thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR', with the proviso that when Alk$^1$ is a bond, Sp$^1$ is a bond;

n is an integer from 0 to 5;

R' is a branched or unbranched $(C_1–C_5)$ chain optionally substituted by one or two groups of —OH, $(C_1–C_4)$ alkoxy, $(C_1–C_4)$ thioalkoxy, halogen, nitro, $(C_1–C_3)$ dialkylamino, or $(C_1–C_3)$ trialkylammonium —A$^-$ where A$^-$ is a pharmaceutically acceptable anion completing a salt;

Ar is 1,2-, 1,3-, or 1,4-phenylene optionally substituted with one, two, or three groups of $(C_1–C_6)$ alkyl, $(C_1–C_5)$ alkoxy, $(C_1–C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined above or a 1,2-, 1,3-, 1,4-, 1,5-, 1,6-, 1,7-, 1,8-, 2,3-, 2,6-, or 2,7-naphthylidene or

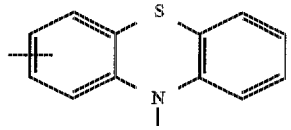

each naphthylidene or phenothiazine optionally substituted with one, two, three, or four groups of $(C_1–C_6)$ alkyl, $(C_1–C_5)$ alkoxy, $(C_1–C_4)$ thioalkoxy, halogen, nitro, —COOR', —CONHR', —O(CH$_2$)$_n$COOR', —S(CH$_2$)$_n$COOR', or —S(CH$_2$)$_n$CONHR' wherein n and R' are as defined above, with the proviso that when Ar is naphthylidene, Z$^1$ is not hydrogen and with the proviso that when Ar is phenothiazine, Sp$^1$ is a bond only connected to nitrogen;

Sp$^2$ is a bond, —S—, or —O—, with the proviso that when Alk$^2$ is a bond, Sp$^2$ is a bond;

Z$^1$ is H, $(C_1–C_5)$ alkyl, or phenyl optionally substituted with one, two, or three groups of $(C_1–C_5)$ alkyl, $(C_1–C_5)$ alkoxy, $(C_1–C_6)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as above;

Sp is a straight or branched-chain divalent or trivalent $(C_1–C_{18})$ radical, divalent or trivalent aryl or heteroaryl radical, divalent or trivalent $(C_3–C_{18})$ cycloalkyl or heterocycloalkyl radical, divalent or trivalent aryl- or heteroaryl-aryl $(C_1–C_{18})$ radical, divalent or trivalent cycloalkyl- or heterocycloalkyl-alkyl $(C_1–C_{18})$ radical or divalent or trivalent $(C_2–C_{18})$ unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, Sp can be additionally substituted by lower $(C_1–C_5)$ dialkylamino, lower $(C_1–C_5)$ alkoxy, hydroxy, or lower $(C_1–C_5)$ alkylthio groups; and Q is =NHNCO—, =NHNCS—, =NHNCONH—, =NHNCSNH—, or =NHO—.

4. The method of claim 3, wherein

Sp$^1$ is a bond, —S—, —O—, —CONH—, —NHCO—, or —NR'— wherein n and R' are as defined in claim 3, with the proviso that when Alk$^1$ is a bond, Sp$^1$ is a bond;

Ar is 1,2-, 1,3-, or 1,4-phenylene optionally substituted with one, two, or three groups of $(C_1–C_6)$ alkyl, $(C_1–C_5)$ alkoxy, $(C_1–C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined in claim 3 or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of $(C_1–C_6)$ alkyl, $(C_1–C_5)$ alkoxy, $(C_1–C_4)$ thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR';

Alk$^2$ is a branched or unbranched $(C_1–C_{10})$ alkylene chain);

$Z^1$ is ($C_1$-$C_5$) alkyl, or phenyl optionally substituted with one, two, or three groups of ($C_1$-$C_5$) alkyl, ($C_1$-$C_4$) alkoxy, ($C_1$-$C_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR'; and Alk$^2$ and Sp$^2$ are together a bond.

5. The method of claim 4, wherein Sp$^1$ is —O—, Alk$^1$ is C$_3$ alkylene, Ar is 1,4-phenylene, and Z$^1$ is C$_1$ alkyl.

6. The method of claim 3, wherein Q is =NHNCO— and Sp is —CH$_2$C(CH$_3$)$_2$—.

7. The method of claim 2, wherein Z is —NHC(=O)— and Sp is —CH$_2$CH$_2$C(CH$_3$)$_2$—.

8. The method of claim 2, wherein Z is —CH=NNHC(=O)— and Sp is —CH$_2$C(CH$_3$)$_2$—.

9. The method of claim 1, wherein the calicheamicin derivative comprises a gamma calicheamicin or an N-acetyl gamma calicheamicin derivative.

10. The method of claim 9, wherein the calicheamicin derivative is present in step (1) in an amount ranging from about 0.025 mg/ml to about 1.0 mg/ml.

11. The method of claim 1, wherein the proteinaceous carrier comprises a humanized monoclonal antibody.

12. The method of claim 11, wherein the humanized monoclonal antibody is present in step (1) in an amount ranging from about 1 mg/ml to about 15 mg/ml.

13. The method of claim 1, wherein the additive of step (1) is present in an amount ranging from 20 to 300 mM.

14. The method of claim 1, wherein the cosolvent comprises propylene glycol in an amount ranging from about 10% to about 60% by volume of the solution.

15. The method of claim 1, wherein the additive in step (1) comprises octanoic acid in an amount ranging from about 20 mM to about 100 mM.

16. The method of claim 1, wherein the cosolvent of step (1) is propylene glycol in an amount of 30% by volume of the solution and the additive of step (1) comprises octanoic acid in an amount of 60 mM.

17. The method of claim 1, wherein the cosolvent is present in step (1) in an amount ranging from about 1% to about 10% by volume of the solution and the additive in step (1) comprises octanoic acid in an amount ranging from about 150 mM to about 300 mM.

18. The method of claim 17, wherein the cosolvent is ethanol.

19. The method of claim 18, wherein the ethanol is present in step (1) in an amount of 5% by volume of the solution and the additive octanoic acid is present in step (1) in an amount of 200 mM.

20. The method of claim 17, wherein the cosolvent of step (1) is propylene glycol in an amount of 5% by volume of the solution and the additive octanoic acid is present in step (1) in an amount of 200 mM.

21. A method for preparing monomeric calicheamicin derivative/carrier conjugates with higher drug loading/yield and decreased aggregation having the formula,

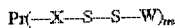

wherein:
Pr is a proteinaceous carrier,
X is a linker that comprises a product of any reactive group that can react with a proteinaceous carrier,
W is the calicheamicin radical formed by removal of the naturally occurring methyl trisulfide group, and
m is a number from 0.5 to 15;
said method comprising the steps of:

(1) incubating a calicheamicin derivative (X—S—S—W) and a proteinaceous carrier (Pr) in a non-nucleophilic, protein-compatible, buffered solution having a pH in the range from about 4.0 to 8.5 which solution further comprises the cosolvent t-butanol, wherein the incubation is conducted at a temperature ranging from about 25° C. to about 37° C. for a period of time ranging from about 15 minutes to about 24 hours to produce a calicheamicin derivative/carrier conjugate; and (2) purifying the calicheamicin derivative/carrier conjugate produced in step (1) to produce a monomeric calicheamicin derivative/carrier conjugate.

22. The method of claim 21, wherein X has the formula Z-Sp wherein:

Sp is a straight or branched-chain divalent of trivalent ($C_1$-$C_{18}$) radical, divalent or trivalent aryl or heteroaryl radical, divalent or trivalent ($C_3$-$C_{18}$) cycloalkyl or heterocycloalkyl radical, divalent or trivalent aryl- or heteroaryl-aryl ($C_1$-$C_{18}$) radical, divalent or trivalent cycloalkyl- or heterocycloalkyl-alkyl ($C_1$-$C_{18}$) radical or divalent or trivalent ($C_2$-$C_{18}$) usaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazolyl, aminocoumarinyl, or phenazinyl and wherein if Sp is a trivalent radical, Sp can be additionally substituted by lower ($C_1$-$C_5$) dialkylamino, lower ($C_1$-$C_5$) alkoxy, hydroxy, or lower ($C_1$-$C_5$) alkylthio groups; and Z is —NHC(=O)—, —CH=NNHC(=O)—, —CH$_2$NHNHC(=O)—, —CH=NNHC(=O)NH—, —CH$_2$NHNHC(=O)NH—, —CH=NNHC(=S)NH—, —CH$_2$NHNHC(=S)NH—, —CH=N—, —CH2NH—, —OC(=O)—, —S—S—,

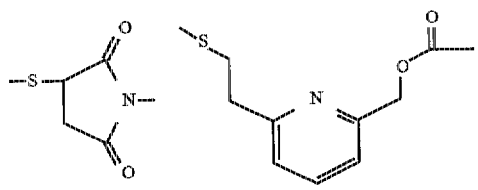

23. The method of claim 21, wherein X has the formula (CO—Alk$^1$—Sp$^1$—Ar—Sp$^2$—Alk$^2$—C(Z$^1$)=Q—Sp)

wherein
Alk$^1$ and Alk$^2$ are independently a bond or branched or unbranched ($C_1$-$C_{10}$) alkylene chain;
Sp$^1$ is a bond, —S—, —O—, —CONH—, —NHCO—, —NR'—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of ($C_1$-$C_5$) alkyl, ($C_1$-$C_4$) alkoxy, ($C_1$-$C_4$)thioalkoxy, halogen, nitro, —COOR', —CONHR', —O(CH$_2$)$_n$COOR', —S(CH$_2$)

$_n$COOR', —O(CH$_2$)$_n$CONHR', or —S(CH$_2$)$_n$CONHR', with the proviso that when Alk$^1$ is a bond, Sp$^1$ is a bond;

n is an integer from 0 to 5;

R' is a branched or unbranched (C$_1$–C$_5$) chain optionally substituted by one or two groups of —OH, (C$_1$–C$_4$) alkoxy, (C$_1$–C$_4$) thioalkoxy, halogen, nitro, (C$_1$–C$_3$) dialkylamino, or (C$_1$–C$_3$) trialkylammonium —A$^-$ where A$^-$ is a pharmaceutically acceptable anion completing a salt;

Ar is 1,2-, 1,3-, or 1,4-phenylene optionally substituted with one, two, or three groups of (C$_1$–C$_6$) alkyl, (C$_1$–C$_5$) alkoxy, (C$_1$–C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined above or a 1,2-, 1,3-, 1,4-, 1,5-, 1,6-, 1,7-, 1,8-, 2,3-, 2,6-, or 2,7-naphthylidene or

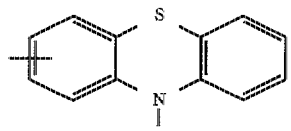

each naphthylidene or phenothiazine optionally substituted with one, two, three, or four groups of (C$_1$–C$_6$) alkyl, (C$_1$–C$_5$) alkoxy, (C$_1$–C$_4$) thioalkoxy, halogen, nitro, —COOR', —CONHR', —O(CH$_2$)$_n$COOR', —S(CH$_2$)$_n$COOR', or —S(CH$_2$)$_n$CONHR' wherein n and R' are as defined above, with the proviso that when Ar is naphthylidene, Z$^1$ is not hydrogen and with the proviso that when Ar is phenothiazine, Sp$^1$ is a bond only connected to nitrogen;

Sp$^2$ is a bond, —S—, or —O—, with the proviso that when Alk$^2$ is a bond, Sp$^2$ is a bond;

Z$^1$ is H, (C$_1$–C$_5$) alkyl, or phenyl optionally substituted with one, two, or three groups of (C$_1$–C$_5$) alkyl, (C$_1$–C$_5$) alkoxy, (C$_1$–C$_5$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined above;

Sp is a straight or branched-chain divalent or trivalent (C$_1$–C$_{18}$) radical, divalent or trivalent aryl or heteroaryl radical, divalent or trivalent (C$_3$–C$_{18}$) cycloalkyl or heterocycloalkyl radical, divalent or trivalent aryl- or heteroaryl-aryl (C$_1$–C$_{18}$) radical, divalent or trivalent cycloalkyl- or heterocycloalkyl-alkyl (C$_1$–C$_{18}$) radical or divalent or trivalent (C$_2$–C$_{18}$) unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, Sp can be additionally substituted by lower (C$_1$–C$_5$) dialkylamino, lower (C$_1$–C$_5$) alkoxy, hydroxy, or lower (C$_1$–C$_5$) alkylthio groups; and Q is =NHNCO—, =NHNCS—, =NHNCONH—, =NHNCSNH—, or =NHO—.

24. The method of claim 23, wherein

Sp$^1$ is a bond, —S—, —O—, —CONH—, —NHCO—, or —NR'— wherein n and R' are as defined in claim 23, with the proviso that when Alk$^1$ is a bond, Sp$^1$ is a bond;

Ar is 1,2-, 1,3-, or 1,4-phenylene optionally substituted with one, two, or three groups of (C$_1$–C$_6$) alkyl, (C$_1$–C$_5$) alkoxy, (C$_1$–C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR' wherein n and R' are as defined in claim 23 or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of (C$_1$–C$_6$) alkyl, (C$_1$–C$_5$) alkoxy, (C$_1$–C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR';

Alk$^2$ is a branched or unbranched (C$_1$–C$_{10}$) alkylene chain);

Z$^1$ is (C$_1$–C$_5$) alkyl, or phenyl optionally substituted with one, two, or three groups of (C$_1$–C$_5$) alkyl, (C$_1$–C$_4$) alkoxy, (C$_1$–C$_4$) thioalkoxy, halogen, nitro, —COOR', —CONHR', —O(CH$_2$)$_n$COOR', —S(CH$_2$)$_n$COOR', —O(CH$_2$)$_n$CONHR', or —S(CH$_2$)$_n$CONHR'; and Alk$^2$ and Sp$^2$ are together a bond.

25. The method of claim 24, wherein Sp$^1$ is —O—, Alk$^1$ is C$_3$ alkylene, Ar is 1,4-phenylene, and Z$^1$ is C$_1$ alkyl.

26. The method of claim 23, wherein Q is =NHNCO— and Sp is —CH$_2$C(CH$_3$)$_2$—.

27. The method of claim 22, wherein Z is —NHC(=O)— and Sp is —CH$_2$CH$_2$C(CH$_3$)$_2$—.

28. The method of claim 22, wherein Z is —CH=NNHC(=O)— and Sp is —CH$_2$C(CH$_3$)$_2$—.

29. The method of claim 21, wherein the calicheamicin derivative comprises a gamma calicheamicin or an N-acetyl gamma calicheamicin derivative.

30. The method of claim 29, wherein the calicheamicin derivative is present in step (1) in an amount ranging from about 0.025 mg/ml to about 1.0 mg/ml.

31. The method of claim 21, wherein the proteinaceous carrier comprises a humanized monoclonal antibody.

32. The method of claim 31, wherein the humanized monoclonal antibody is present in step (1) in an amount ranging from about 1 mg/ml to about 15 mg/ml.

33. The method of claim 21, wherein the t-butanol is present in step (1) in an amount ranging from about 10% to about 25% by volume of the solution.

34. The method of claim 21, wherein the t-butanol is present in step (1) in an amount of 15% by volume of the solution.

* * * * *